US006845268B2

(12) United States Patent
Hill et al.

(10) Patent No.: US 6,845,268 B2
(45) Date of Patent: Jan. 18, 2005

(54) RATE STABILIZATION WITH MAINTENANCE OF INTRINSIC VENTRICULAR RESPONSE

(75) Inventors: Michael R. S. Hill, Minneapolis, MN (US); Michael F. Hess, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 300 days.

(21) Appl. No.: 10/090,053

(22) Filed: Feb. 28, 2002

(65) Prior Publication Data

US 2003/0163169 A1 Aug. 28, 2003

(51) Int. Cl.[7] ............................................. A61N 1/365
(52) U.S. Cl. ........................................................ 607/25
(58) Field of Search .......................... 607/5, 9, 11, 14, 607/15, 25, 27

(56) References Cited

U.S. PATENT DOCUMENTS

| 3,857,399 A | 12/1974 | Zacouto ................... 128/419 P |
| 4,163,451 A | 8/1979 | Lesnick et al. ....... 128/419 PG |
| 4,467,810 A | 8/1984 | Vollmann ............. 128/419 PG |
| 4,503,857 A | 3/1985 | Boute et al. .......... 128/419 PG |
| 4,562,841 A | 1/1986 | Brockway et al. .... 128/419 PG |
| 4,932,407 A | 6/1990 | Williams ................. 128/419 D |
| 4,941,471 A | 7/1990 | Mehra ................... 128/419 PG |
| 4,953,551 A | 9/1990 | Mehra et al. ........... 128/419 D |
| 5,117,824 A | 6/1992 | Keimel et al. .......... 128/419 D |
| 5,163,427 A | 11/1992 | Keimel .................... 128/419 D |
| 5,174,288 A | 12/1992 | Bardy et al. ............ 128/419 D |
| 5,188,105 A | 2/1993 | Keimel .................... 128/419 D |
| 5,261,400 A | 11/1993 | Bardy ............................ 607/5 |
| 5,545,185 A | 8/1996 | Denker ........................ 607/14 |
| 5,814,085 A | 9/1998 | Hill .............................. 607/14 |
| 6,285,907 B1 | 9/2001 | Kramer et al. ................. 607/9 |
| 6,708,062 B2 * | 3/2004 | Ericksen et al. ............... 607/9 |

* cited by examiner

*Primary Examiner*—George Manuel
(74) *Attorney, Agent, or Firm*—Michael C. Soldner; Girma Wolde-Michael

(57) ABSTRACT

A device implemented software system for use with atrial and/or ventricular rate stabilization to adjust DDD/R rate stabilization while maintaining intrinsic ventricular response timing to overdrive the intrinsic sinus (atrial) rate. Specifically, the algorithm is directed toward maintaining ventricular activation/contraction sequence while improving atrial and ventricular hemodynamics. Generally, the PAV interval is prolonged subsequent to a sensed premature beat. In an ultimate embodiment, the algorithm enables extension of the PAV interval subsequent to a non-conducted premature atrial event. The extension of the PAV interval allows for the simultaneous smoothing of the atrial and ventricular rates.

7 Claims, 4 Drawing Sheets

RATE STABILIZATION WITH MAINTENANCE OF INTRINSIC VENTRICULAR RESPONSE

FIELD OF THE INVENTION

The invention relates generally to implantable medical devices that pace the heart. More particularly, it relates to a timing method for pacing the heart so that the cardiac rhythm is stabilized in the presence of a premature ventricular contraction (PVC).

BACKGROUND OF THE INVENTION

A healthy human heart may be able to maintain its own intrinsic rhythm often for the lifetime of the patient. Yet, even a healthy human heart will sometimes exhibit some irregularities, such as premature ventricular contractions (PVCs) and paroxysmal atrial tachycardias (PATs), among others, that upset the heart's AV sequential contractions, momentarily diminishing cardiac output. Some of these momentary interruptions in cardiac rhythm seldom require medical intervention. On the other hand, individuals may be born with or develop cardiac arrhythmias that require medical intervention. Some of these patients may benefit from drug therapy, while others will require an implantable medical device (IMD), such as a pacemaker or a pacer cardiac defibrillator (PCD), among others.

Generally, pacers are used to treat bradyarrhythmias, whereas PCDs are used to treat tachyarrhythmias. By properly timing the delivery of pacing pulses, the heart will contract in proper rhythm, thereby restoring its efficiency as a pump. PVCs or PACs, however, may occur in some patients and interrupt the paced cardiac rhythm. Such interruptions may, at times, result in atrial or ventricular tachyarrhythmias. Atrial fibrillation may, in turn, induce irregular ventricular heart rhythms by processes not yet fully understood. Such induced ventricular arrhythmias compromise pumping efficiency even more drastically than atrial arrhythmias.

PCDs are used with patients who already exhibit signs of an irritable heart. PCDs differentiate between various types of ventricular tachycardias (VTs), such as non-life-threatening VTs and life-threatening ventricular fibrillation (VF), and treat them differently. With these devices it is even more important to prevent the development of a VT, since these arrhythmias can lead to a life-threatening arrhythmia.

Other cardiac rhythm management systems treat congestive heart failure (CHF). Congestive heart failure can be treated by biventricular, coordinated pacing therapy that provides pacing pulses to both right and left ventricles in a sequential fashion. Such devices also must ensure against any irregularities in rhythm that sometimes occur due to interactions between the device and the heart. Even though a congestive heart failure patient may have adequate ventricular coordination and cardiac output in the presence of a normal sinus rhythm, when an atrial or ventricular premature event occurs, biventricular coordination may cease, seriously worsening cardiac function.

Rate smoothing algorithms are not new to the art of preventing arrhythmias or to the maintenance of AV synchrony. Such software systems have been implemented in the Medtronic® Gem® DR with ventricular rate stabilization in the DDD/R modes and the Medtronic® Jewel® AF with atrial rate stabilization in the DDD mode.

Over the years, a variety of pacing modes have been developed to respond to changes in spontaneous heart activity. One of the earliest of these is disclosed in U.S. Pat. No. 3,857,399, issued to Zacouto. Zacouto provides a system in which the underlying heart rhythm is used to control the onset of pacing, but not the pacing rate. The onset of pacing in Zacouto can occur after an interval either shorter or longer than the underlying physiologic interval.

U.S. Pat. No. 4,163,451 issued to Lesnick et al discloses a pacemaker having an overdrive-pacing mode. It provides for initiation of cardiac pacing at an interval shorter than the detected cardiac interval. The purpose of this pacing modality is to provide a method of tachycardia treatment.

U.S. Pat. No. 4,562,841 issued to Brockway et al discloses a dual chamber pacemaker, in which a gradual increase and decrease of pacing intervals occurs in response to changes in the underlying heart rate. However, adjustment of the pacing interval is primarily based on the atrial rate, rather than the ventricular. There appears to be no provision, however, for adjusting the atrial escape interval as a function of the measured escape interval following a PVC.

U.S. Pat. No. 4,503,857 issued to Boute et al discloses a cardiac pacemaker that drops the ventricular rate to the lower limit of a "physiologic rate band" and thereafter gradually lengthens the escape interval in response to an equation until a programmed rate is attained. This modality is referred to as "flywheel" pacing, and is intended to prevent abrupt changes in pacing rate.

U.S. Pat. No. 4,467,810 issued to Vollmann discloses a dual chamber pacemaker that employs a fall-back pacing mode in which ventricular pacing intervals are gradually incremented in response to a high atrial rate. The alteration of escape intervals is intended to terminate atrial tachycardias.

In U.S. Pat. No. 4,941,471, Mehra discloses a cardiac pacemaker which generates stimulus pulses and senses the occurrence of natural heartbeats in a patient. The pacemaker provides for a mode of pacing that tracks naturally conducted depolarizations, and responds to PVCs by gradually increasing pacing cycle until a predetermined lower rate is reached. In U.S. Pat. No. 5,814,085, Hill reveals a cardiac pacemaker with a rate stabilization pacing mode. The pacemaker varies the increment following a cycle ending in a sensed depolarization as a function of the underlying heart rate and may additionally vary the increment as a function of the prematurity of the most recently sensed depolarization relative to the preceding depolarization.

Denker, in U.S. Pat. No. 5,545,185, discloses a pacemaker for preventing tachyarrhythmia by measuring the cardiac cycle length and detecting the occurrence of a PVC more than a predefined amount between consecutive cycles. When a normal heart beat does not occur within a predefined period of time after such an abrupt change in cycle length, the resulting compensatory pause is eliminated by a cardiac pacer applying an appropriately timed electrical pulse to produce a ventricular depolarization.

Kramer, in U.S. Pat. No. 6,285,907, discloses a cardiac rhythm management system that includes techniques for computing an indicated pacing interval, AV delay, or other timing intervals. The indicated pacing interval is used to time the delivery of biventricular coordination therapy even when ventricular heart rates are irregular, such as in the presence of atrial fibrillation.

Current dual chamber implementations may actually shorten the PAV interval via a rate-adaptive AV response in response to the rate stabilization algorithm, thereby forcing a ventricular pacing output. In addition, a compensatory pause after a PVC temporarily prolongs VA conduction. This pause usually results in a paced atrial and ventricular response. From a ventricular point of view, such an operation is not ideal, because it results in the following sequence: an intrinsic ventricular depolarization using the Purkinje system, a PVC from an ectopic focus in the ventricle, followed by a paced beat usually from a pacing electrode located in the apex of the right ventricle—and, in biventricular pacing, from a fourth focus, an electrode located in the upper posterior portion of the left ventricle. The activation of three or four separate foci within such a short period of time works counter to the maintenance of intrinsic activation. From a clinical point of view, such activation may actually exacerbate the dispersion of refractoriness and/or potential for block/reentry.

In a similar fashion, the sequence described above is not ideal from an atrial point of view. Paced and intrinsic atrial depolarizations produce different hemodynamic responses due to the following activation/contraction coupling sequences. The following sequence may lead to altered hemodynamics such as, for example, atrial sense-ventricular sense (AS-VS), premature AS leading to an intrinsically conducted VS, followed by an atrial pace-ventricular pace (AP-VP). Atrial activation from widely separated foci may detrimentally affect the atrial tissue, making it more prone to atrial fibrillation. Atrial fibrillation, in turn, results in decreased ventricular filling and output. While many paced patients may tolerate such a decrease, the effect on heart failure patients is usually less advantageous.

In view of the above, there is a need for an algorithm that maintains intrinsic, rather than paced, ventricular activity while, at the same time, maintaining various rate stabilization methods, specifically in a dual chamber operation.

SUMMARY OF THE INVENTION

The present invention can be used in conjunction with atrial and/or ventricular rate stabilization software systems algorithms, that operate to adjust DDD/R timing to overdrive the intrinsic sinus (atrial) rate. Generally, the present invention is directed toward maintaining ventricular activation/contraction sequence and improving atrial and ventricular hemodynamics.

The present invention proposes a prolongation of the PAV interval subsequent to a sensed premature beat, whether atrial or ventricular, in conjunction with the calculation of the paced escape interval used by the rate stabilization, or other pacing prevention algorithm. The increased duration of the PAV interval is calculated and based on whether the ventricular event prior to the PVC was sensed or paced. The prolongation of the PAV interval would allow an intrinsic ventricular depolarization to occur, thereby attaining and maintaining ventricular regularization and AV synchronization. The first PAV interval has the longest extension, with subsequent PAV intervals becoming shorter until the programmed PAV interval is reached. Such a method provides a transition back to a fully paced or sensed rhythm to match the rhythm prior to the PVC, without abrupt ventricular rate changes.

Alternatively, the algorithm also allows for an extension of the PAV interval subsequent to a non-conducted premature atrial event. Without such an extension, atrial rate stabilization would result in a brief elevation of the ventricular rate. Since some patients may become symptomatic due to such changes in ventricular rate, use of a prolonged PAV would result in a lesser change in the ventricular rate than would occur with a fixed PAV interval. Such a method also achieves the electrophysiological goal of atrial rate stabilization.

The extension of the PAV interval allows for the simultaneous smoothing of the atrial and ventricular rates. At the same time, the extended PAV interval that results in a less dramatic change in the ventricular rate as compared to the atrial rate, may also result in the reduction of patient symptoms.

DETAILED DESCRIPTION OF THE DRAWINGS

Figure 1:
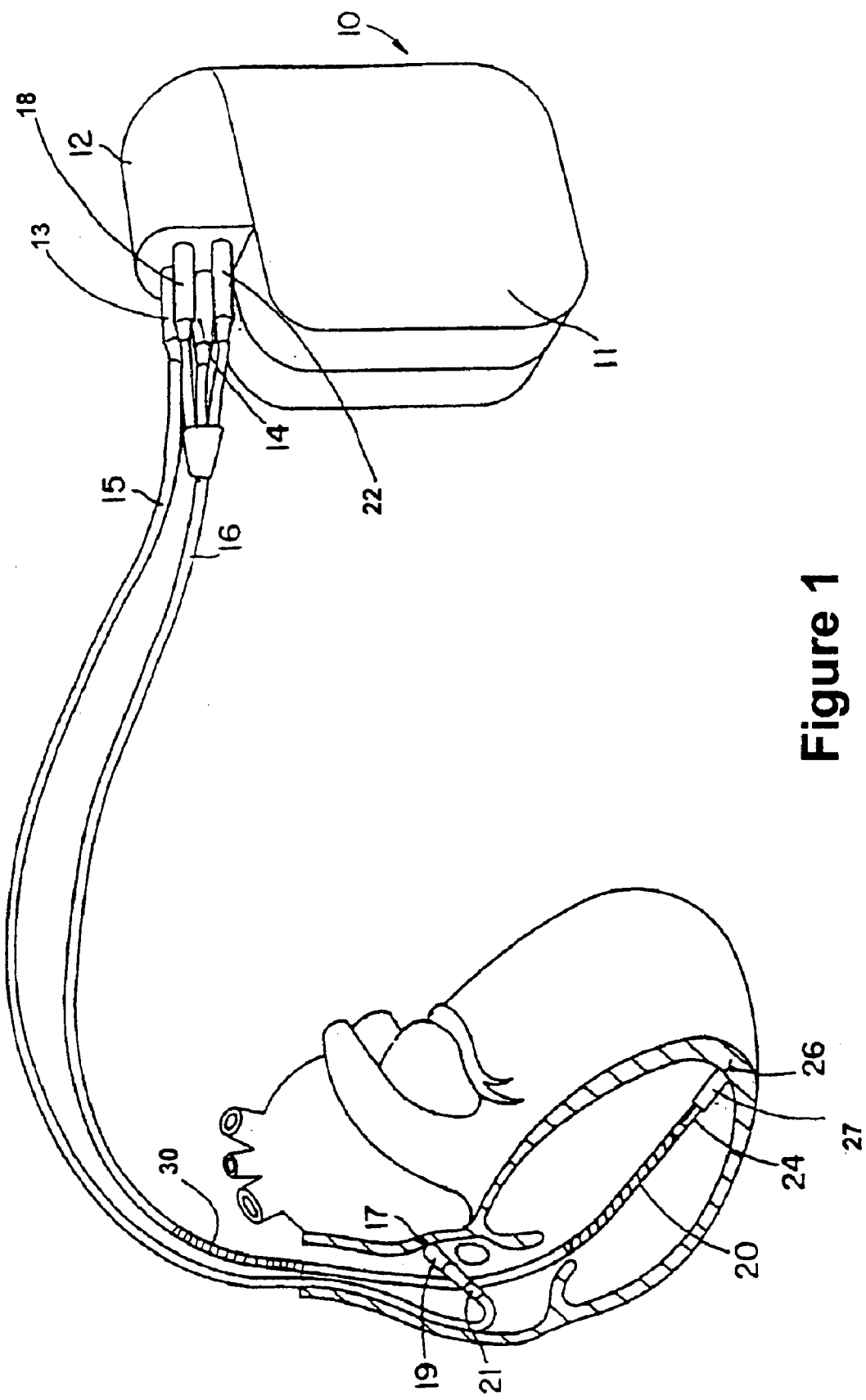
FIG. 1 is an illustration of a PCD type system according to the present invention.

Referring now to FIG. 1, there are illustrated a defibrillator 10, leads 15 and 16 making up the PCD type system of the present invention. The leads shown are for illustrative purposes only, it being noted that other specific forms of leads are within the scope of this invention. See, for example, U.S. Pat. Nos. 4,932,407 and 5,174,288, as well as U.S. Pat. No. 5,261,400, all of which are incorporated by reference. Ventricular lead 16 as illustrated has, located adjacent to the distal end, an extendable helix electrode 26 and a ring electrode 24, the helix electrode being mounted retractably within an insulative head 27. Electrodes 24 and 26 are used for bipolar ventricular pacing and for sensing ventricular depolarizations. While electrodes 24 and 26 may be used for bipolar pacing and sensing, electrode 26 may be used in conjunction with the surface of device casing 10, which surface acts as a common or indifferent electrode in what is termed unipolar operation. Ventricular lead 16 also carries a coil electrode 20, sometimes referred to as the RV (right ventricular) coil, for delivering defibrillation and/or cardioversion pulses. Coil electrode 20 is positioned on lead 16 so that when the distal tip is at the apex of the ventricle, coil 20 is positioned in the right ventricle. Lead 16 may also carry, optionally, an SCV coil 30, positioned in the subclavian vein, which can be used for R wave sensing and/or applying cardioversion pulses. Lead 16 carries respective concentric coil conductors (not shown), separated from one another by appropriate means such as tubular insulative sheaths and running the length of the lead for making electrical connection between the PCD device 10 and respective ones of electrodes 20, 24, 26 and 30.

Atrial lead 15 as illustrated has, located adjacent to the distal end, an extendable helix electrode 17 and a ring electrode, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 10, which surface acts as a common or indifferent electrode in what is termed unipolar operation. Note that, in this example, atrial lead 15 is not equipped with coils for use in the sensing and delivery of cardioversion of defibrillation pulses. This is not meant to preclude the inclusion of such applications that may be used advantageously with the present invention.

An implantable PCD type device, or defibrillator 10, is shown in combination with atrial and ventricular leads, with the lead connector assembly 13, 14, 18, and 22 being inserted into the connector block 12 of the device 10. A specific example of a defibrillation pulse generator that may be used in conjunction with the present ventricular lead is disclosed in U.S. Pat. No. 4,953,551. Other PCD type units can be used; reference is made to U.S. Pat. Nos. 5,163,427 and 5,188,105 as disclosing illustrative forms of apparatus for delivering cardioversion and defibrillation pulses. As used herein, the term "PCD type" device refers to any device that can apply both pacing therapy and shock therapy for controlling arrhythmias.

Figure 2:
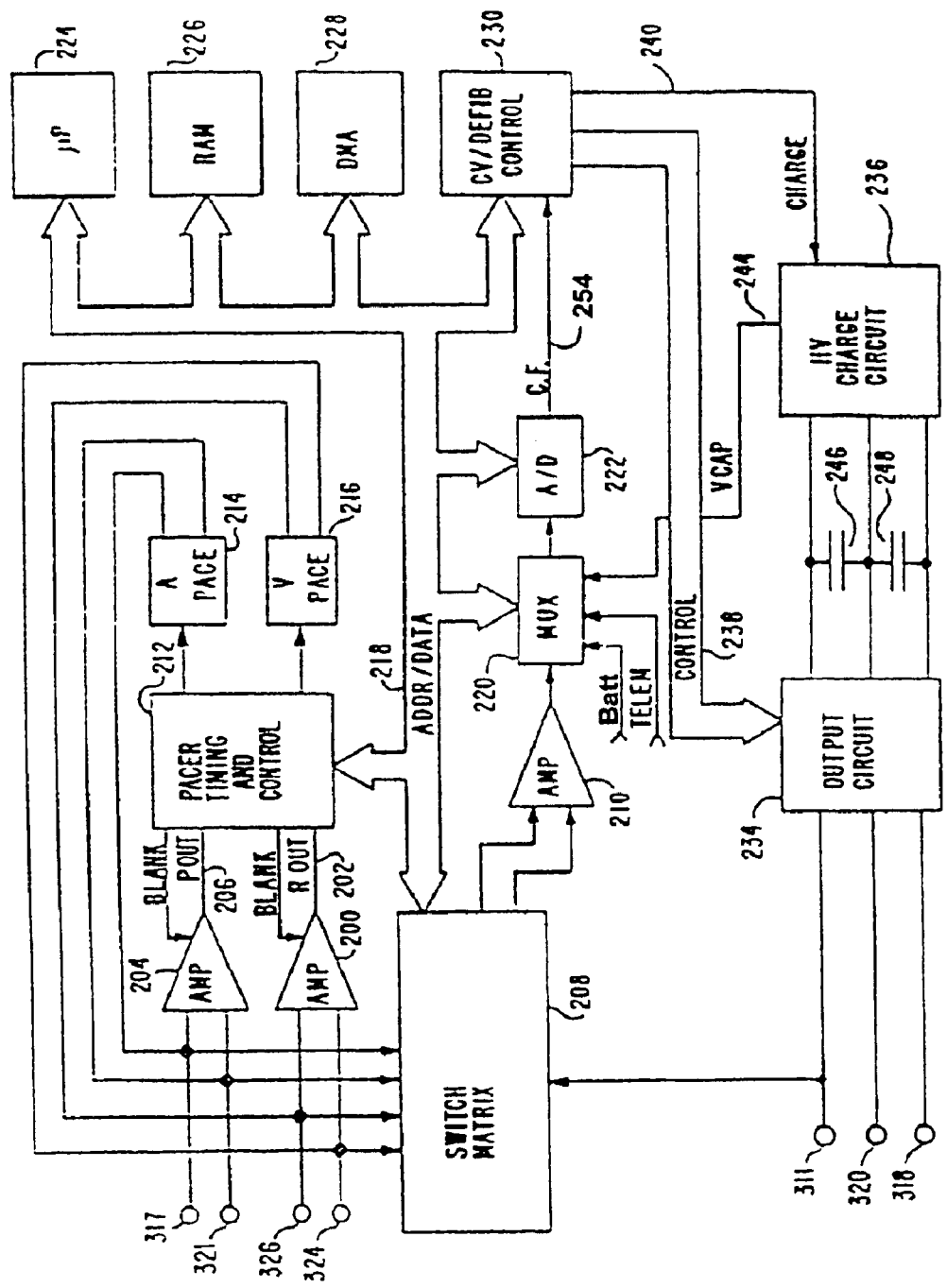
FIG. 2 is a block, functional diagram of a PCD type device adapted to carry out the features of the present invention.

FIG. 2 is a functional schematic diagram of an implant able pacemaker/cardiover-ter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the implant able pacemaker/cardioverter/defibrillator. Electrode 320 corresponds to electrode 20 and is a defibrillation electrode located in the right ventricle. Electrode 318 corresponds to electrode 30 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of R-R intervals, P-P intervals, P-R intervals, and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

For the sake of simplicity, the remaining portions of the drawing will not be described in detail because they do not pertain to the present invention.

Figure 3:
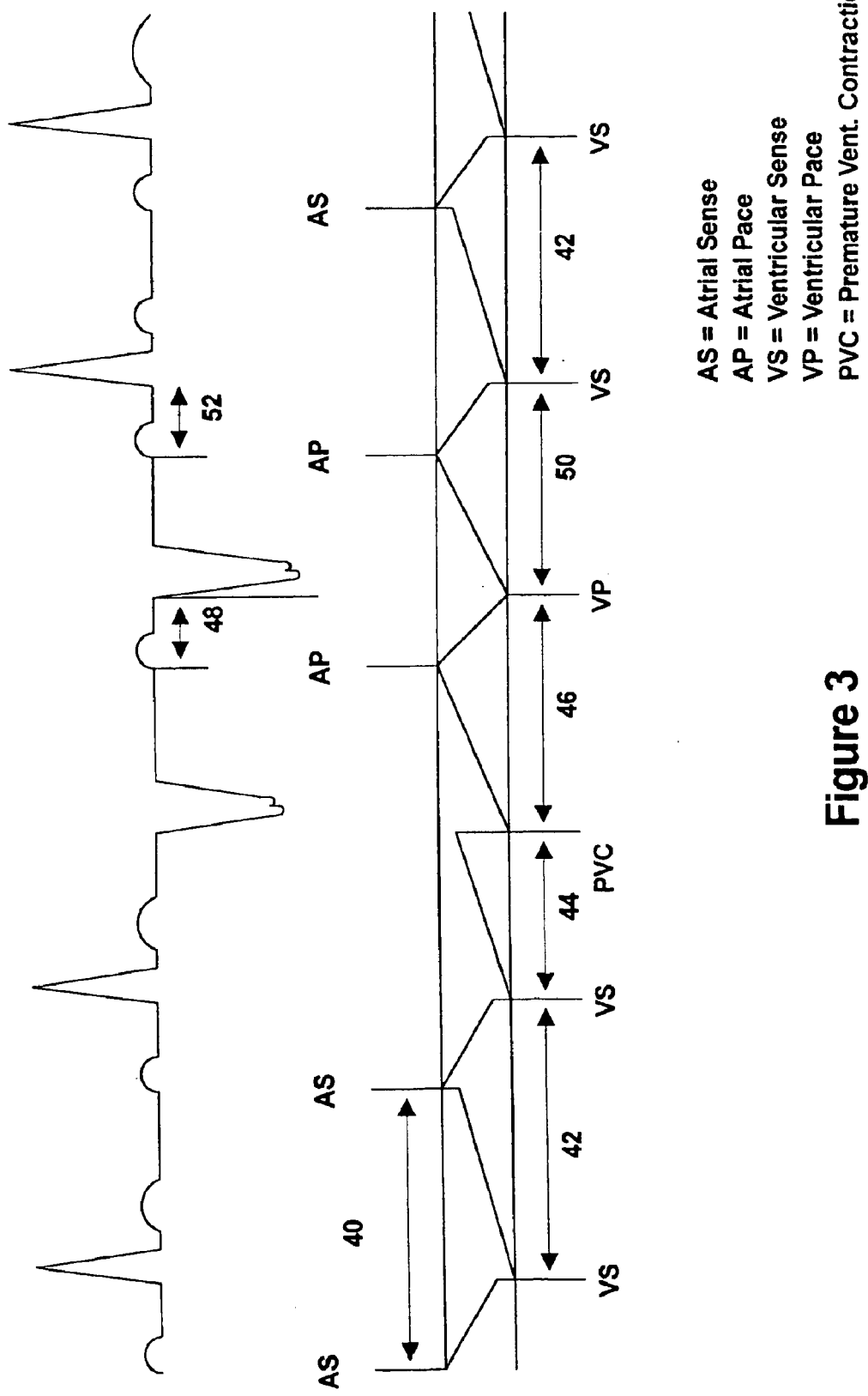
FIG. 3 is a timing diagram that illustrates the operation of a rate stabilization algorithm.

FIG. 3 is a timing diagram that illustrates the operation of a rate stabilization algorithm. Typically, a rate stabilization algorithm such as the ventricular rate stabilization (VRS) algorithm implemented in the Medtronic® Gem® DR shortens the AV interval following either a premature atrial or ventricular beat, because rate adaptive AV features are typically in effect and the post-PAC/PVC rate typically increases over the pre-PAC/PVC rate.

Interval 40 corresponds in duration to interval 42, representing the patient's atrial rhythm is sinus driven and sensed atrial depolarizations are conducted to the ventricles. interval 44 terminating with a premature ventricular contraction (PVC), interrupts the regular sinus driven rhythm. In such cases, the VRS calculates a new paced ventricular escape interval 46 that approximates interval 42, to maintain rate stability in so far as this is possible. The VRS also subtracts a shortened PAV interval 48 from interval 46 and the pacing circuitry emits an atrial output pulse at the start of interval 48. Interval 50 may terminate in a ventricular sensed event, with PAV interval 52 starting with a paced atrial event. Paced atrial events may and often will continue for several more cycles, until the sinus rate recovers from the interruption caused by the PVC. Similarly, ventricular paced events may also continue until the AV node recovers and allows normal AV conduction.

The embodiment in FIG. 3 demonstrates the effect of the ventricular sequence, VS, PVC, and VP, on patient hemodynamics. For ventricular VRS applications, this sequence is not ideal because it does not maintain normal AV conduction and may exacerbate the dispersion of refractoriness in the AV node and His/Perkinje conduction system. Further, it may increase the potential for block or retrograde re-entry in the ventricular tissue.

In atrial rate stabilization (ARS) implementations in which a premature atrial beat occurs (not shown), a disadvantageous effect on patient hemodynamics may occur. A sequence of AS-VS, premature atrial beat (PAB)-VS, followed by AP-VP may also alter patient hemodynamics. More importantly, such a sequence may affect the atrial substrate, thereby making it more prone to atrial fibrillation. Additionally, such a sequence may diminish ventricular fill capacity, resulting in a decrease in cardiac output which might affect heart failure patients. For all these reasons, maintenance of intrinsic ventricular activation is critical during ARS/VRS implementations.

Figure 4:
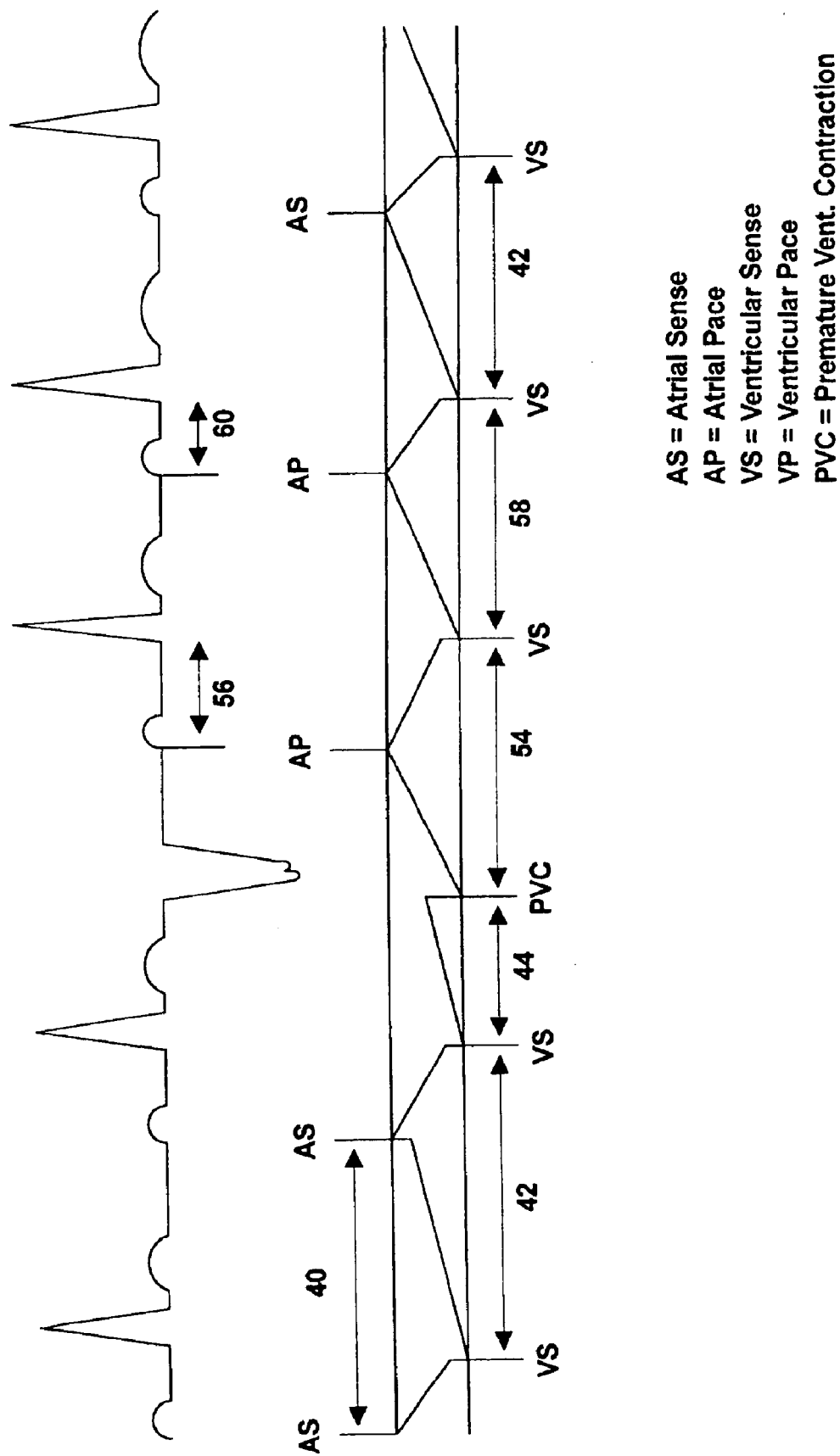
FIG. 4 is a timing diagram that displays the operation of the present invention in conjunction with a rate stabilization algorithm.

FIG. 4 is a timing diagram that displays the operation of the present invention in conjunction with a rate stabilization algorithm. In the preferred embodiment, the algorithm calculates a PAV interval, after a premature event, which will maintain an intrinsic ventricular rate that is very close to the previous sensed ventricular rate.

Interval 40 in FIG. 4 corresponds in duration to interval 42, representing a condition in which the patient's atrial rhythm is sinus driven and sensed atrial depolarizations are conducted to the ventricles. Interval 44, terminating with a premature Ventricular contration (PVC), interrupts the regular sinus driven rhythm. In this embodiment, however, the VRS calculates a new paced ventricular escape interval 54 that approximates interval 42, to maintain rate stability in so far as this is possible. The VRS also subtracts a new, lengthened PAVn interval 56 from interval 54 and the pacing circuitry omits an atrial output pulse at the start of interval 56. The result of lengthened PAV interval 56 is a VS event at end of interval 54, although it could have been a ventricular pace as described below.

The duration of PAVn depends on the ventricular rhythm (paced or sensed) in place prior to the premature event. Thus, if the previous rhythm were intrinsic, the PAVn would be longer to promote ventricular conduction, whereas the PAVn would be shorter if the previous ventricular rhythm was paced. It should be noted that the PAVn of interval 60 is shorter than that of interval 56. The PAVn will continue to shorten until the PAV that was in effect prior to the premature event is reached, or an intrinsic sinus event occurs, consistent with the sequence of intervals 58 to 42. The ARS algorithm similarly calculates a lengthened PAVn to maintain the previous ventricular rhythm, that is, prior to the premature atrial beat.

The present invention, when used in conjunction with VRS or ARS, ensures that the focus for depolarization of the ventricle and/or atrium is restored as quickly as possible following a premature atrial or ventricular event. In this way, the potential detrimental effects of a rate stabilization algorithm will be avoided.

In a bi-ventricular embodiment, which has sensing from either ventricular site, the present invention would enable selection of the right or left ventricular site to determine the sensed or paced PAVn. Alternatively, the same bi-ventricular embodiment could adjust the V-V interval to effect the same rate smoothing in both the right and left ventricles simultaneously, even if a sensed event occurs in only one ventricular chamber.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A device-implemented software system for maintaining ventricular activation or contraction sequence to improve atrial and ventricular hemodynamics, the system comprising:

means for prolonging a first PAV interval subsequent to a sensed premature beat;

means for decrementing PAV intervals arising after said first PAV interval; and means for identifying at least one of said PAV intervals that is equal to a programmed PAV interval.

2. The system of claim 1 wherein said means for prolonging includes means for extending the PAV interval subsequent to a non-conducted premature atrial event.

3. The system of claim 1 wherein said means of decrementing includes means for controlling subsequent PAV intervals to become shorter until said PAV interval is equal to the programmed PAV interval.

4. The system of claim 1 wherein said means for prolonging further includes means for simultaneous smoothing of the atrial and ventricular rates.

5. The system of claim 1, further comprising means for determining a rhythm occurring prior to the sensed premature beat, wherein the prolonging means prolongs the first PAV interval in response to the determined rhythm.

6. A method for maintaining ventricular activation or contraction sequence to improve atrial and ventricular hemodynamics, the method comprising:

prolonging a first PAV interval subsequent to a sensed premature beat; and decrementing PAV intervals arising after said first PAV interval; and identifying at least one of said PAV intervals that is equal to a programmed interval.

7. The system of claim 5, wherein the first PAV interval is prolonged for a first time period in response to the determined rhythm being an intrinsic rhythm and for a second time period, not equal to the first time period, in response to the determined rhythm being other than an intrinsic rhythm.

* * * * *